US009511368B2

(12) United States Patent
Kim et al.

(10) Patent No.: US 9,511,368 B2
(45) Date of Patent: Dec. 6, 2016

(54) TRANSPORTING, TRAPPING AND ESCAPING MANIPULATION DEVICE FOR MAGNETIC BEAD BIOMATERIAL COMPRISING MICRO-MAGNETOPHORETIC CIRCUIT

(71) Applicant: The Industry & Academic Cooperation in Chungnam National University (IAC), Daejeon (KR)

(72) Inventors: Cheolgi Kim, Daejeon (KR); Byeonghwa Lim, Daejeon (KR); Venu Reddy, Daejeon (KR); XingHao Hu, Daejeon (KR); KunWoo Kim, Daejeon (KR); Benjamin B. Yellen, New York, NY (US)

(73) Assignee: The Industry & Academic Cooperation in Chungnam National University (IAC) (KR)

( * ) Notice: Subject to any disclaimer, the term of this patent is extended or adjusted under 35 U.S.C. 154(b) by 338 days.

(21) Appl. No.: 14/013,751

(22) Filed: Aug. 29, 2013

(65) Prior Publication Data

US 2015/0064764 A1    Mar. 5, 2015

(51) Int. Cl.
 *G01N 1/40* (2006.01)
 *B03C 1/033* (2006.01)
 (Continued)

(52) U.S. Cl.
 CPC ............ *B01L 3/502761* (2013.01); *B03C 1/01* (2013.01); *B03C 1/0335* (2013.01); *B03C 1/288* (2013.01);
 (Continued)

(58) Field of Classification Search
 CPC ................. B01L 3/502761; B01L 2300/0816; B01L 2400/043; B01L 2300/0864; B01L 2200/0652; B01L 2200/0668; B03C 1/0335; B03C 1/288; B03C 1/01; B03C 2201/18; B03C 2201/26; B03C 1/23; B03C 1/24; G01N 1/4077; H01F 1/12; H01F 1/14; H01F 1/14708; H01F 1/14716; H01F 1/15316; H01F 1/16; H01F 41/34
See application file for complete search history.

(56) References Cited

U.S. PATENT DOCUMENTS 5,981,297 A    11/1999  Baselt
6,730,204 B2 *  5/2004  Mariella, Jr. ........... B03C 5/026
                                                           204/547
(Continued)

FOREIGN PATENT DOCUMENTS

KR    2008-0009825    1/2008

OTHER PUBLICATIONS

Anandakumar et al., Translocation of bio-functionalized magnetic beads using smart magnetopheresis, Biosensors and Bioelectrics, 26, 2010, pp. 1755-1758.*

(Continued)

*Primary Examiner* — David C Mellon
(74) *Attorney, Agent, or Firm* — Lucas & Mercanti, LLP

(57) ABSTRACT

A device for transporting, trapping and escaping a single biomaterial using a magnetic structure, and a method of transporting, trapping and escaping of the single biomaterial using the same are provided, and a method is provided for controlling movement and direction of the single biomaterial including soft magnetic micro structure and magnetic structure in a linear, square storage, apartment type, radial soft magnetic micro structure. Accordingly, the device for transporting, trapping and escaping a single biomaterial and the method for transporting, trapping and escaping single biomaterial using the same can control movement on the lap-on-a-chip with increased precision and ease, by using magnetic force, and thus can be advantageously used in the field of magneto-resistive sensor, or categorization of single cells or biomolecules.

17 Claims, 14 Drawing Sheets

(51) Int. Cl.
  *B03C 1/28*   (2006.01)
  *B03C 1/01*   (2006.01)
  *B01L 3/00*   (2006.01)

(52) U.S. Cl.
  CPC . *B01L 2200/0652* (2013.01); *B01L 2200/0668* (2013.01); *B01L 2300/0816* (2013.01); *B01L 2300/0864* (2013.01); *B01L 2400/043* (2013.01); *B03C 2201/18* (2013.01); *B03C 2201/26* (2013.01); *G01N 1/4077* (2013.01)

(56) References Cited

U.S. PATENT DOCUMENTS

| | | | | |
|---|---|---|---|---|
| 6,790,330 B2* | 9/2004 | Gascoyne | ............... | B03C 5/026 |
| | | | | 204/547 |
| 6,858,439 B1* | 2/2005 | Xu | ...................... | B01J 19/0046 |
| | | | | 204/409 |
| 6,875,329 B2* | 4/2005 | Washizu | ................. | B03C 5/026 |
| | | | | 204/547 |
| 7,081,192 B1* | 7/2006 | Wang | ................ | B01L 3/502761 |
| | | | | 204/547 |
| 7,204,139 B2* | 4/2007 | Takayama | ............ | B01F 5/0646 |
| | | | | 73/204.26 |
| 8,399,229 B2* | 3/2013 | Sooryakumar | ... | B01L 3/502761 |
| | | | | 210/222 |
| 2011/0234342 A1* | 9/2011 | Kim | ........................ | B03C 1/253 |
| | | | | 335/284 |
| 2015/0267726 A1* | 9/2015 | Prakash | ............ | B01L 3/502792 |
| | | | | 137/803 |

OTHER PUBLICATIONS

R. Venu, et al., On-Chip Manipulation and Trapping of Microorganisms . . . , Microfluid Nanofluid, 2012.

* cited by examiner

TRANSPORTING, TRAPPING AND ESCAPING MANIPULATION DEVICE FOR MAGNETIC BEAD BIOMATERIAL COMPRISING MICRO-MAGNETOPHORETIC CIRCUIT

BACKGROUND OF THE INVENTION

1. Field of the Invention

The present invention relates to a device for transporting, trapping and escaping biomaterial using micro-magnetophoretic circuit and magnetic structures, and a method for transporting, trapping and escaping biomaterial using the same.

2. Description of the Related Art

It is difficult for existing laboratory systems to promptly process a large amount of bio-information poured as the human genome project has been completed and the post-genomic era has arrived. Accordingly, biological identification systems for investigation of vital phenomena, development of new drug and diagnosis are being developed into the forms of a micro-Total Analysis System (μ-TAS) and a lab-on-a-chip, which are for analyzing a sample accurately and conveniently in a short time with less amount of the sample on the basis of microfluidics.

Since most of biochemical samples to be analyzed area present in the form of a solution, a technique to translocate the liquid sample can be the most important factor. The microfluidics is just the field of microfluidic flow control, and is the field of studying and developing essential technologies that form the foundation of commercialization of the μ-TAS and the lab-on-a-chip.

The μ-TAS is a system that totally carries out chemical and biological experiment and analysis, which go through a plurality of experimental steps and reactions, on a single unit present in a single experimental stand. This μ-TAS includes a sample collection area, a microfluidic circuit, a detector and a controller for controlling them.

Meanwhile, the lab-on-a-chip means a laboratory within a chip or a laboratory on a chip, in which a microfluidic channel of nanoliter or smaller is fabricated using a material such as plastic, glass and silicon and a liquid sample of only several nanoliters is translocated through the microfluidic channel, whereby existing experimental or study procedures can be carried out quickly.

Realization of μ-TAS or a lab-on-a-chip capable of quickly carrying out analysis for sharply increasing bio-information can be effectively achieved when it is combined with proper bioassay methods.

Since the binding procedure of these biomolecules cannot be observed directly, markers capable of generating a detectable signal is used. In general, fluorescent material, radioactive material, enzyme or magnetic particle is used as the marker. In this detection method, it is important to generate a high sensitive signal so as to enable recognition of a trace amount of detection molecule.

In particular, target materials to be analyzed are recently diversified in the fields of development of new drug and diagnosis with development of synthetic chemistry and life science, and these target materials are very high in cost and are not easily obtained. Therefore, there is increasing needs for cost reduction through the trace analysis.

Among detection methods to ensure generation of high sensitive signal, various methods using magnetic particles have been reported.

Patent document 1 discloses a method in which recognition agents selectively immobilizing target molecules are bound to magnetizable particles and a magnetoresistive or magnetostrictive response of these bound particles to a magnetic field sensor is observed to detect the particles.

There has been developed a method of detecting a desired DNA by immobilizing a DNA to a Giant Magnetoresistive (GMR) device and measuring a magnetic flux of a magnetic particle, which is used as a marker, as a value of resistance variation. Also, there is a method, in which in order to find whether magnetic particles are immobilized by a biological recognition procedure, a residual magnetism and a magnetic susceptibility from a magnetic particle of iron oxide ($Fe_3O_4$) are measured from the magnetic particles using a Superconducting Quantum Interference Device (SQUID) to thereby recognize a detection molecule. The above described methods show high sensitive detection ability in biomolecule detection.

Those mentioned above are referred to as planar array types which immobilize receptor molecules on a planar substrate for analysis, with the externally-prepared sample. Additionally, since the biomolecules obtained in the above manner are those that are extracted from several thousands to several hundred and thousand cells and supplied, the characteristic of individual cells can hardly be known.

Although there exist apparatuses for separating biomolecules based on microbeads, they have limited ability to carry out complex operation since the microbeads are fabricated with a permanent magnet or an electromagnet of 5 mm or greater. Also, current technology for biomolecule translocation is not sufficient to control at nano-scale. Further, systems for bioassay are generally difficult in manufacture and high in cost, and also generate heat that may kill biological individuals. Furthermore, movement of magnetic media using this system is not smoother than the micro magnetic device for biomolecule translocation in accordance with the present invention.

In addition, since conventional magnetic tweezers and microneedles have only one tip, they can translocate only one magnetic medium and cannot translocate media in neighboring group.

Meanwhile, compared to the concepts like electric circuit and bubble microfluid, the concept of circuit, which can guide the digital flow of small packets of matter such as single cell and/or protein-coded colloidal particles, along patterned circuitry have not yet been demonstrated.

Patent document 2 discloses a microfluidic system comprising magnetic bead extracting device and a microfluid system including the same, adapted for the purpose of biomolecule separation and purification in the conventional microfluidic system. The microfluidic system selectively guides only the magnetic beads in the sample fluid flowing a passage of the sample fluid channel and collecting the same in the buffer solution chamber, and discharging the rest through the sample fluid outlet, thereby obtaining purified magnetic beads without having to perform separate washing process.

The inventors designed basic magnetophoretic circuit required to precisely control the flow of magnetic structures including magnetic beads and magnetic nanoparticles and magnetically-labelled single biomaterials along magnetically patterned circuitry.

The magnetic structures represent very flexible system for transporting and separating biological materials, and recent years have witnessed great progress in systems for controlling the movement of magnetic structures in micro scale. However, there have not been any demonstrations of the equivalent circuitry for controlling particle currents in fluids in a manner analogous to electronic circuits.

The inventors of the subject application discovered that matter currents defined above lithographically patterned magnetic tracks follow an equivalent form of Ohm's law, in which the driving frequency in this system plays the analogous role of voltage in electrical system. The inventors have also implemented more complex circuit elements, such as a matter rectifier, which transports matter only along preferred directions, and have used combinations of these fundamental circuit elements to demonstrate both focusing of magnetic structure to a magnetoresistive sensor, the storage capacitor and on demand release of single cells in localized apartments.

Transport of colloidal particles with magnetic micropatterns exploits non-linear dynamic phenomena to precisely control the motion of magnetic structures in massively parallel.

The micro-pattern's periodic potential energy landscape is modulated by an external time-varying magnetic field to shift the regions of potential energy minima and transport magnetic structures along programmable pathways.

The inventors of the present application perceived the potential ability to control the movement of magnetic structures using changes in magnetic field and utilize the same, and completed the subject invention by developing a device for controlling transporting, trapping and escaping of biomaterials using micro magnetophoretic circuit and magnetic structures based on soft magnetic micro structures.

RELATED ART

Patent document 1: U.S. Pat. No. 5,981,297
Patent document 2: Korean Patent Publication No. 2008-0009825

SUMMARY OF THE INVENTION

An object of the present invention is to provide a device for transporting, trapping and escaping magnetic structure on a substrate, with a micro magnetophoretic circuit.

Another object of the present invention is to provide soft magnetic micro structure in various forms which constitute the above device.

Yet another object of the present invention is to provide a method for transporting, trapping and escaping biomaterials using the above device.

Yet another object of the present invention is to provide a method for transporting, trapping and escaping individual cell, which is advantageously utilized in the research of individual cell differentiation, cancer cell evolution, cell aging and cell heterogeneity.

DETAILED DESCRIPTION OF THE INVENTION

To achieve the objects mentioned above, the present invention provides A device for transporting, trapping and escaping a single biomaterial using magnetic structure, which may include a magnetic force generator which applies a magnetic force, a soft magnetic microstructure including a magnetic structure transporting portion having a plurality of half-disc patterns and magnetic segment patterns connected in series, and a magnetic structure storage having a plurality of half-disc patterns and magnetic segment patterns connected in series along an inner wall of square-shaped disc pattern, and a magnetic structure which moves along the outer circumference of the half-disc patterns and the magnetic segment patterns of the magnetic structure transporting portion and the magnetic structure storage of the soft magnetic microstructure, wherein the magnetic structure is conjugated with a single biomaterial.

In another embodiment, a soft magnetic microstructure is provided, which may include a magnetic structure transporting portion having a plurality of half-disc patterns and magnetic segment patterns connected in series, and a magnetic structure storage having a plurality of half-disc patterns and magnetic segment patterns connected in series along an inner wall of square-shaped disc pattern.

In another embodiment, an apartment-type soft magnetic structure is provided, which may include an independent magnetic structure transporting portion having a plurality of half-disc patterns and magnetic segment patterns connected in series, and an apartment-type pattern having two or more of the soft magnetic microstructures of claim 16 connected to each other at a predetermined intervals.

In yet another embodiment, a radial-type soft magnetic microstructure is provided, which may include a plurality of magnetic structure transporting portions in radial array, which comprises a plurality of half-disc patterns and magnetic segment patterns connected in series, and which is so patterned that an arbitrary half-disc pattern on the magnetic structure transporting portions is connected to one or more of the magnetic structure transporting portions.

In yet another embodiment, a method for transporting, trapping and escaping a magnetic structure is provided, which may include transporting the magnetic structure along a magnetic structure transporting portion, by applying magnetic field to a magnetic field generator (step 1); and trapping the magnetic structure transported at step 1 into a magnetic structure storage, while maintaining strength and direction of the applied magnetic field (step 2).

According to various embodiments, a device for transporting, trapping and escaping biomaterial is able to not only control the translocation and direction of the magnetic structure such as magnetic beads or magnetic nanoparticles existing on a board, but also selectively separate single biomaterial such as biomolecule such as DNA, protein, or virus, bacteria, or single cell, and thus is advantageously utilized in the research of individual cell differentiation, cancer cell evolution, cell aging and cell heterogeneity which involves the use of single biomaterial.

BRIEF DESCRIPTION OF THE DRAWINGS

FIG. 7 illustrates a digital concept of the process of switching controlling the transporting of a conjugate including therein magnetic structure and biomaterial using micro current, in which FIG. 7(a) shows transporting along a pathway before switching, FIG. 7(b) shows immediately before switching to a different pathway, and FIG. 7(c) shows transporting along a pathway after switching;

FIG. 8 illustrates escaping the trapped magnetic structure using 10-100 mA current, in which FIG. 8(a) illustrates magnetic structure approaching a boundary of escape, FIG. 8(b) shows magnetic structure at the escaping boundary, FIG. 8(c) shows magnetic structure immediately after escaping, and FIG. 8(d) shows magnetic structure moving after escaping;

FIG. 9 illustrates soft magnetic microstructure form capturing a biomaterial in 10×10 apartment type array (e.g., 100 arrays) by two dimensional (2D) switching control, in which FIG. 9(a) is an overall schematic view, FIG. 9(b) shows the device controlling switching to the lines A to J (FIG. 7), FIG. 9(c) shows the device controlling switching to the rows 1 to 10, and FIG. 9(d) shows device to escape the individual cells from the apartment (FIG. 8);

FIG. 12 shows lens circuit for focusing matter for sensing applications, in which FIG. 12(a) shows the integrated MR sensor and matter focusing, FIG. 12(b) shows particles collected into the center of the lens under clockwise rotation of the magnetic field, FIG. 12(c) shows particles dispersed out of the center node under a counter-clockwise driving field, and FIG. 12(d) shows the time response of the MR signal for the focusing and defocusing pathways;

PREFERRED EMBODIMENTS

Throughout the description, the terms that represent the moving direction of magnetic structure may be so defined that, on a linear X axis and a Y axis orthogonal to the X axis in the coordinate plane, the term "positive X-direction" refers to a direction that faces the right-hand side of the coordinates, while the term "negative X-direction" refers to a direction on the same line as the "positive X-direction" but with opposite direction. Further, the term "positive Y-direction" refers to a direction on the orthogonal coordinates that faces the upper portion of the Y axis, while the term "negative Y-direction" refers to a direction on the same line as the "positive Y-direction", but with opposite direction.

In one embodiment, a device for transporting, trapping and escaping a single biomaterial using magnetic structure is provided, which may include, a magnetic force generator;

a soft magnetic microstructure including a magnetic structure transporting portion having a plurality of half-disc patterns and magnetic segment patterns connected in series, and a magnetic structure storage having a plurality of half-disc patterns and magnetic segment patterns connected in series along an inner wall of square-shaped disc pattern, and a magnetic structure which moves along the outer circumference of the half-disc patterns and the magnetic segment patterns of the magnetic structure transporting portion and the magnetic structure storage of the soft magnetic microstructure, in which the magnetic structure is conjugated with a single biomaterial.

Figure 1:
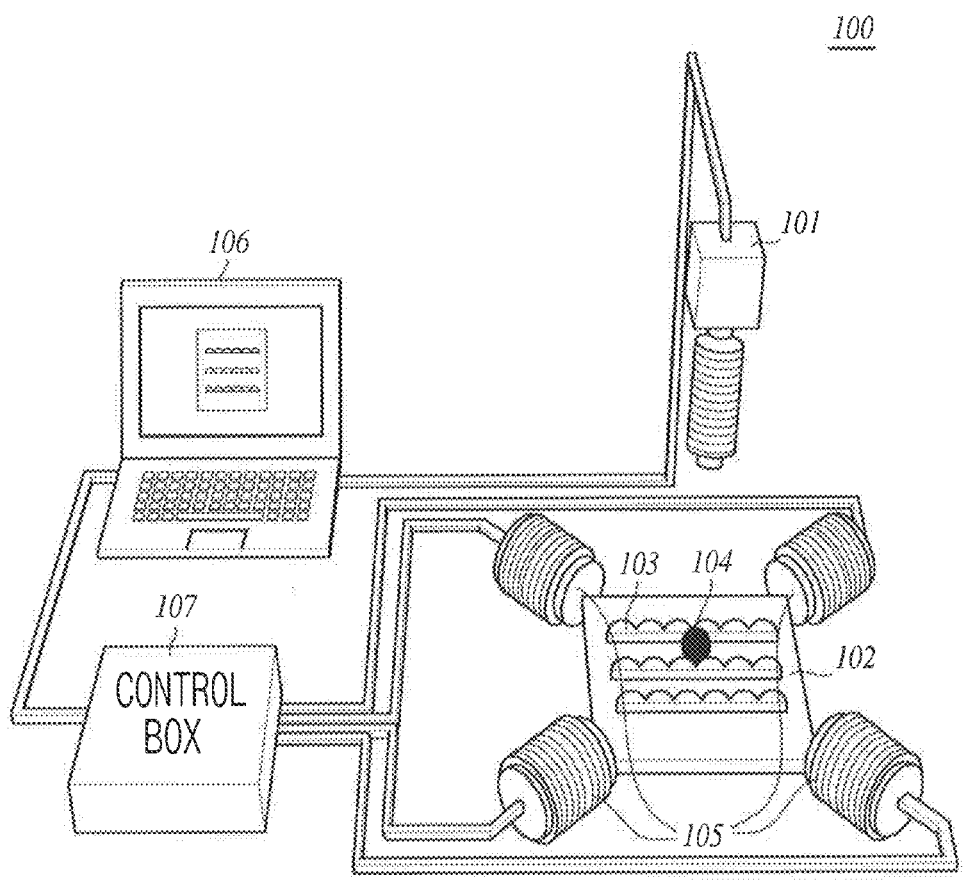
FIG. 1 is a schematic view of a device for transporting, trapping and escaping magnetic structure, which includes a magnetic force generator; a soft magnetic microstructure; and a magnetic structure.

Referring to FIG. 1, a device 100 for transporting, trapping and escaping the magnetic structure includes a magnetic force generator 105 using solenoid coil, which is arranged adjacent to a substrate 102 having a soft magnetic microstructure 103 and a magnetic structure 104, an electric current controller 107 to control whether or not to apply magnetic force and also to control rotation of the magnetic field, and a magnetic structure configured to receive influence of the applied magnetic force to move the structure phase which is formed by repetitious connection of a plurality of half-disc patterns (see FIG. 5, a') and magnetic segment patterns (see FIG. 5, a'') of the soft magnetic microstructure transporting portion or storage.

Further, a camera may be arranged above the substrate to observe the movement of the magnetic structure.

In one embodiment, the magnetic force generator may magnetize the soft magnetic microstructure and magnetic structure or control the strength of direction of the magnetic field formed by the applied magnetic force.

It is possible to generate the magnetic force at the magnetic force generator, by arranging a device including one or more solenoid coils near to a substrate which includes the soft magnetic microstructure therein and applying the magnetic force or generating rotating magnetic field using a device for controlling the flow of electric current on the solenoid coil.

In one embodiment, the magnetic structure transporting portion and the magnetic structure storage may be structures which are so patterned as to be connected to each other integrally.

In one embodiment, the magnetic structure transporting portion and storage may be structures which are so patterned that one terminal end of the magnetic structure transporting portion is connected to one terminal end of the magnetic structure storage to form one complete semicircular structure.

When the connecting portions of the two patterns form one complete semicircle, the magnetic particles can easily migrate from the transporting portion to the storage.

In one embodiment, the soft magnetic microstructure may be formed by soft magnetic thin film patterning including NiFe, CoFe, NiCo, Fe, Ni, Co, and alloy of the same.

To be specific, the soft magnetic microstructure may be deposited with a conventional method used to deposit metal thin film on a glass or silicon substrate by sputtering, or the like, in which controlling movement of the magnetic structure with increased efficiency can be provided, because the material such as NiFe, CoFe, NiCo, Fe, Ni, Co, or alloy including the above has soft magnetism so that it maintains magnetism as long as external magnetic field is applied.

Figure 2:
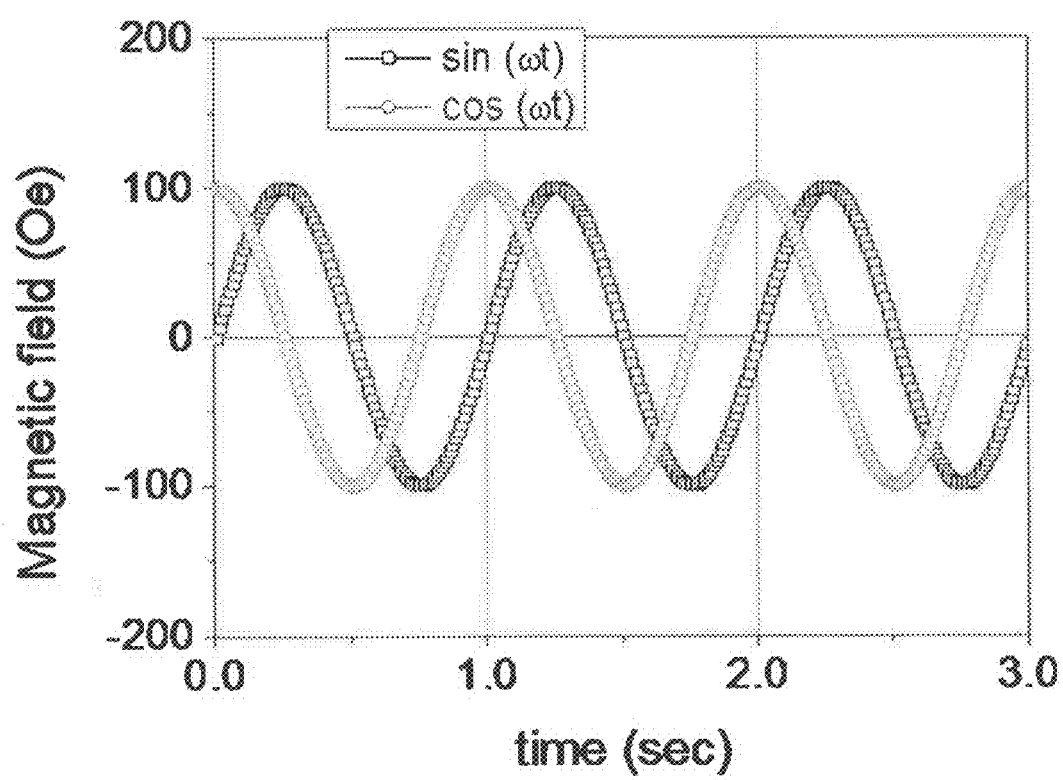
FIG. 2 shows time variations of magnetic field generated in two pairs of magnetic field generators of FIG. 1 to obtain rotating magnetic field.

When external magnetic field is applied to the disc pattern of soft magnetic microstructure, induction magnetic field is thus generated from the disc pattern of soft magnetic microstructure, and, referring to FIG. 2, it is possible to control the size of generated force with relatively increased accuracy, because the magnetization curve in circular pattern has relatively linear proportional relationship with magnetic field depending on the applied magnetic field, than the magnetization curve of a thin film.

In one embodiment, the rate of the diameter of the half-disc and the length of the magnetic segment is preferably 1-10:1.

When the rate of the diameter of the half-disc to the length of the magnetic segment is less than 1, the magnetic structure has less stable migration and it is also harder to control the movement. When the rate of the diameter of the half-disc to the length of the magnetic segment is above 10, it is inefficient in terms of energy because this requires too high magnetic field strength to move the magnetic structure.

The half-disc and magnetic segment in successive structure forms potential wells at predetermined unit of distance of the movement of the magnetic structure, thereby allowing more precise control.

Figure 3:
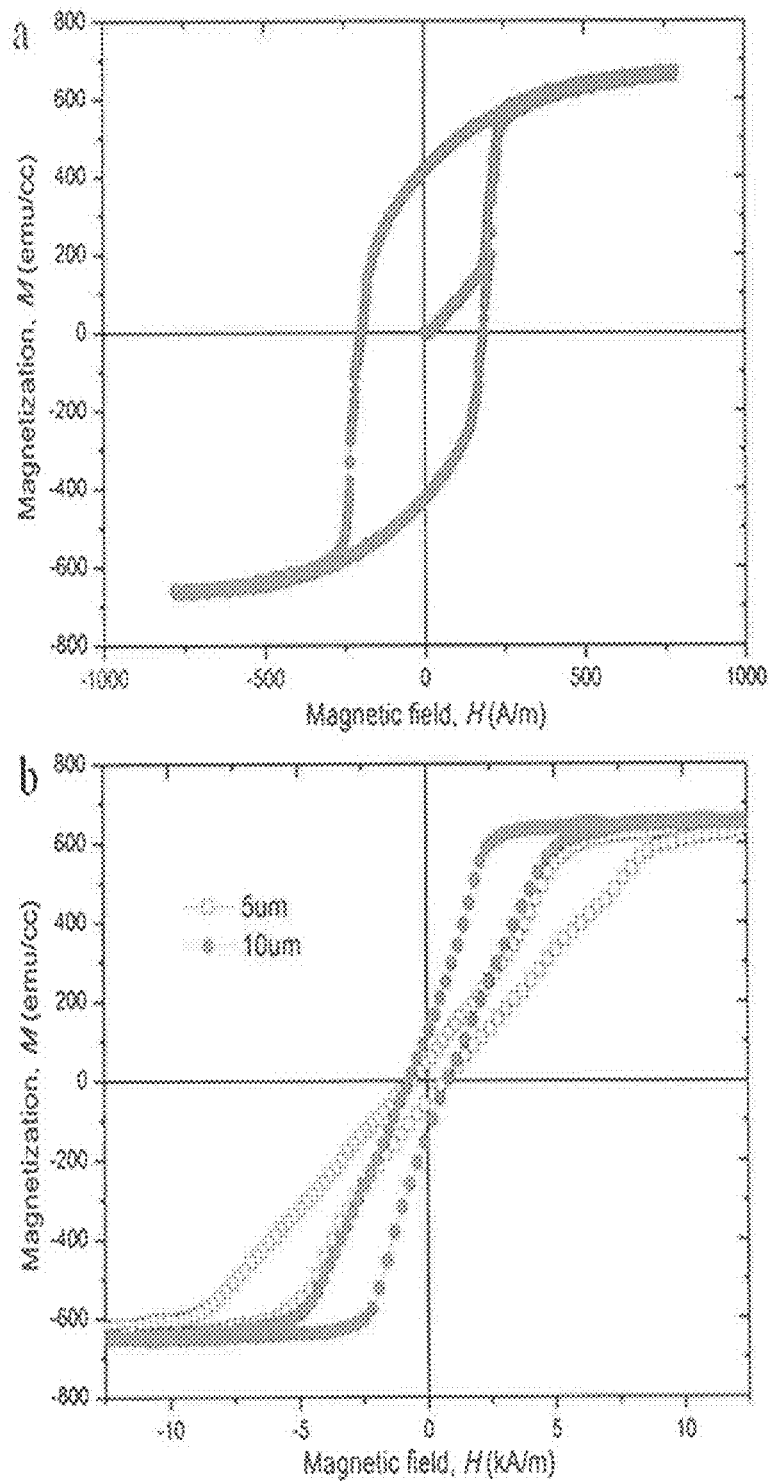
FIG. 3(a) is magnetic hysteresis curve of general NiFe thin film which is 100 nm in thickness.
FIG. 3(b) is magnetic hysteresis curve of disc pattern of NiFe thin film which is 100 nm in thickness.
Figure 4:
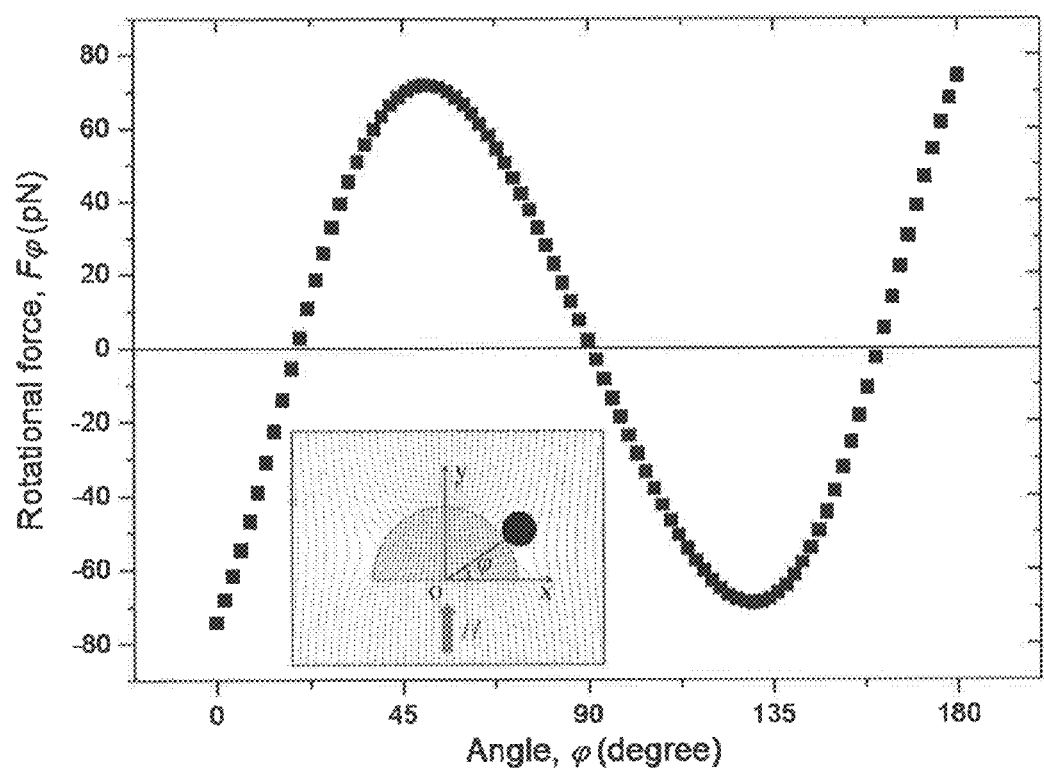
FIG. 4 is a graph plotting rotating force of superparamagnetic structure on a semicircular, soft magnetic microstructure disk, in 7.96 kA/m magnetic field applied by the angle function of external magnetic field.

Further, the soft magnetic microstructure and the magnetic structure are magnetized by the application of external magnetic field, and there is generated a rotating force that rotates along the outer circumference of the half-disc pattern of the soft magnetic microstructure of the magnetic structure according to the angle of rotation of the external magnetic field. The rotating force of the magnetic structure in relation with the variation of the angle of rotation of the magnetic field is illustrated in FIG. 3.

In one embodiment, the magnetic structure may use a material with superparamagnetism which is magnetizable by the application of magnetic field.

In one embodiment, the magnetic structure may use magnetic bead or magnetic nanoparticle, but not limited thereto.

Further, in one embodiment, the biomaterial may use a material either existent in, or originated from a living organism, and more specifically, may use, for example, a biomolecule selected from a group consisting of DNA, protein and virus; bacteria; and cell.

In one embodiment, the magnetic structure may use a functional groupbindable to single biomaterial such as one or more biomolecule selected from a group consisting of DNA, protein and virus, or single bacteria or single cell, or magnetic structure with modified surface so as to have antibodybindable by antigen-antibody reaction. Accordingly, the device according to one embodiment may be used for the purpose of separating a single biomaterial such as one or more biomolecule selected from a group consisting of DNA, protein and virus, or single bacteria, or cell of living body.

In one embodiment, it is possible to modify the surface of magnetic structure by attaching a functional group such as amino group or carboxyl group, before the separation by magnetic field, and bound with a biomaterial such as a single cell or biomolecule. As a result, it is possible to indirectly control the movement of biomaterial by controlling selective binding to the magnetic structure and movement.

In one embodiment, the binding between the magnetic structure and the biomaterial may be amide binding or ester binding.

As the surface of the magnetic structure is modified with a functional group such as amino group or carboxyl group, the functional group is reacted with the functional group inside molecule or cell, to thus allow amide or ester binding to occur.

By the binding explained above, it is possible to induce selective binding with antigen-antibody reaction with the biomaterial targeted for separation, and separate intended biomaterial by applying magnetic field.

In one embodiment, the magnetic structure forms binds to the biomaterial to thus form a conjugate-structure. The conjugate-structure formed as explained above may include, for example, one selected from a group consisting of magnetic bead-DNA conjugate, magnetic bead-protein conjugate, magnetic bead-virus conjugate, magnetic bead-cell conjugate, magnetic bead-bacteria conjugate, magnetic nanoparticle-cell conjugate and magnetic nanoparticle-bacteria conjugate, but not limited thereto.

In one embodiment, the magnetic structure under influence of magnetic field formed by the application of magnetic force moves along an outer circumference of the half-disc pattern of the magnetic structure transporting portion, and at a connecting portion with the magnetic structure storage, continues to move to the advancing direction, inward the storage.

Figure 5:
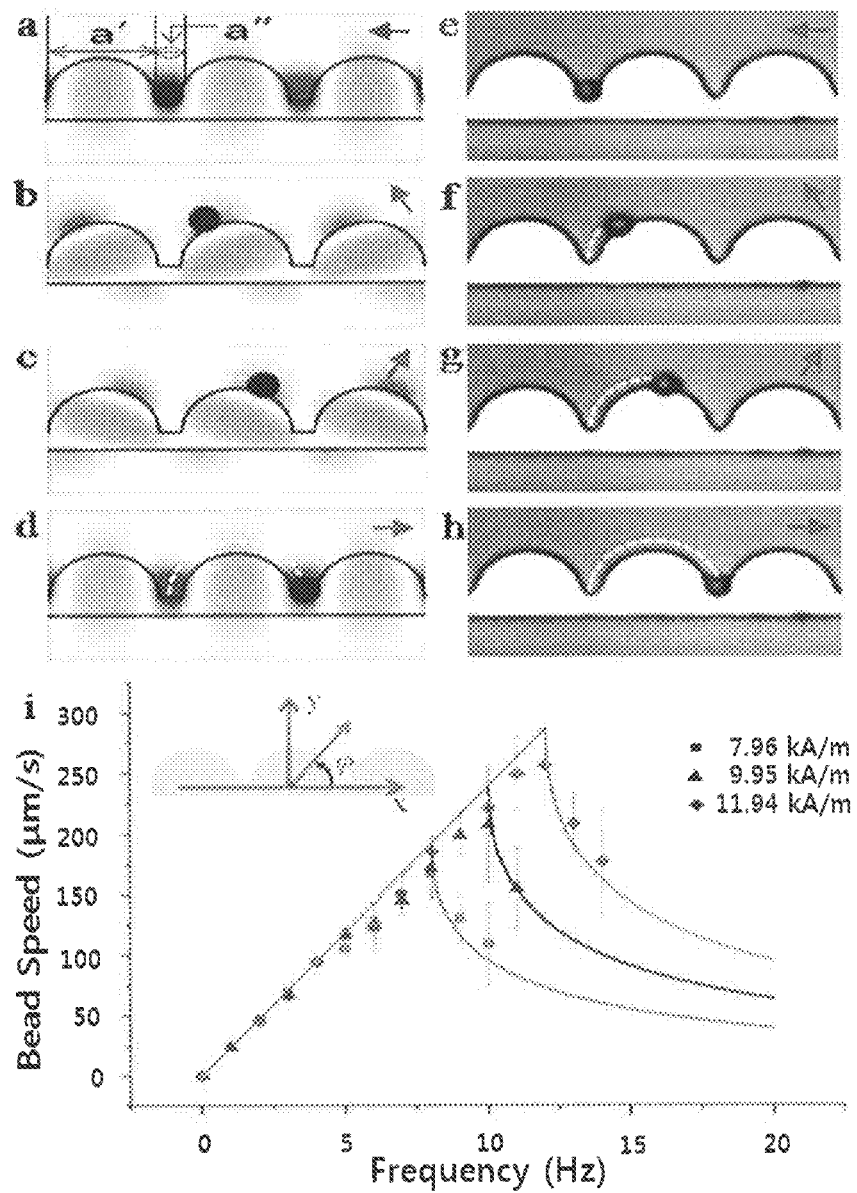
FIGS. 5(a) to 5(d) are graphs representing the potential energy landscape for a 2.8 μm diameter magnetic structure (magnetic permeability=0.62) around the a half-disc track (10 μm diameter, 100 nm thick NiFe film) at the field angles of 180°, 120°, 60°, and 0° under a clockwise 7.96 kA/m rotating field in which blue and red colors designate the energy minima and maxima, respectively.
FIGS. 5(e) to 5(h) are corresponding experimental images and FIG. 5(i) is a graph of linear motion of magnetic structure representing the velocity versus frequency relationship for the movement of magnetic structure for rotating field strengths of 7.96 kA/m, 9.95 kA/m, and 11.94 kA/m.
Figure 6:
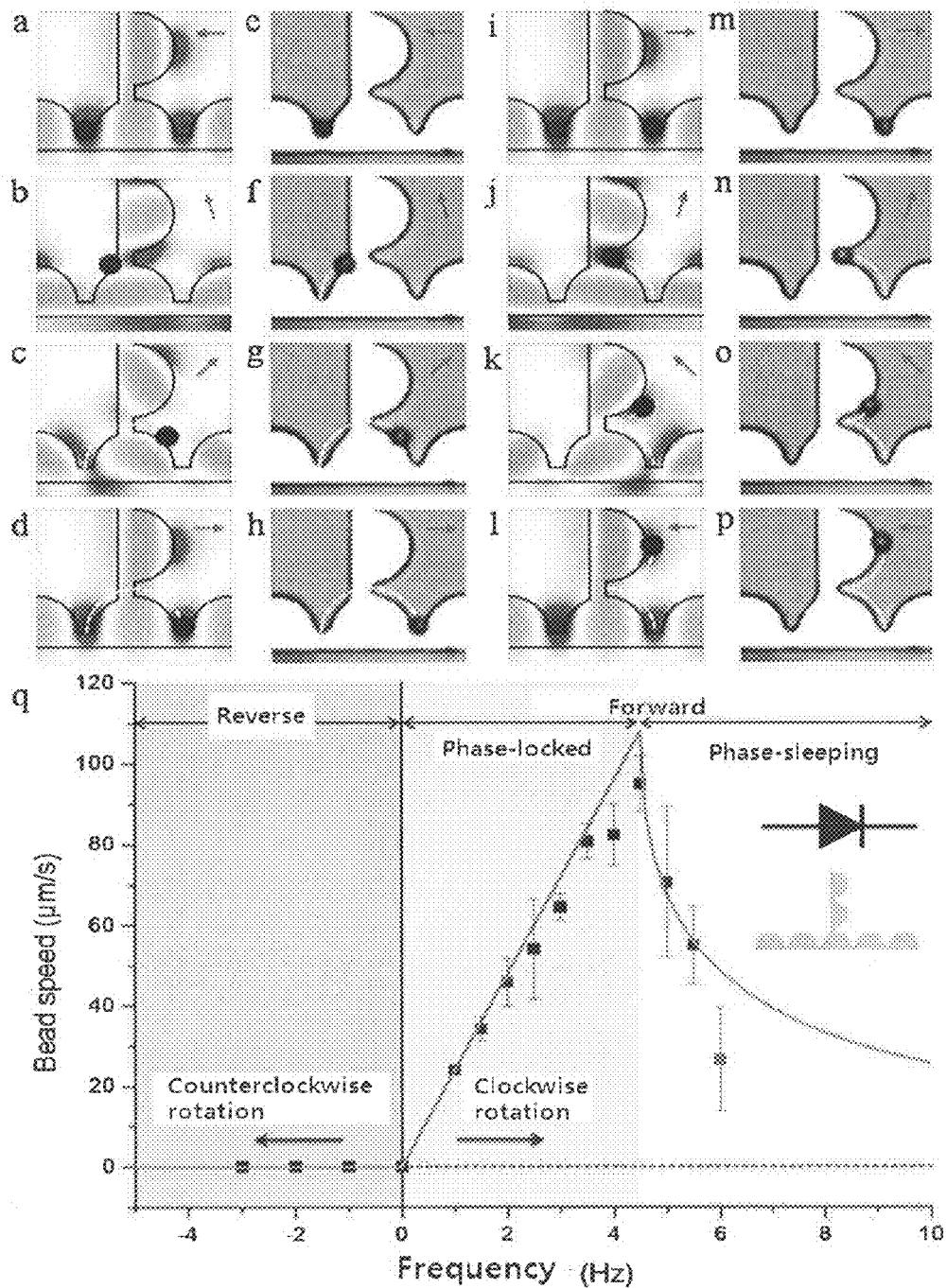
FIGS. 6(a) to 6(d) are graphs representing the potential energy landscape for a 2.8 μm diameter magnetic structure (magnetic permeability=0.62) around the a half-disc track (10 μm diameter, 100 nm thick NiFe film) at the field angles of 180°, 120°, 60°, and 0° under a clockwise 7.96 kA/m rotating field in which blue and red colors designate the energy minima and maxima, respectively.
FIGS. 6(e) to 6(h) are corresponding experimental images.
FIGS. 6(i) to 6(l) are graphs representing the potential energy landscape for the reverse conditions for field angles of 0°, 75°, 135°, and 180°.
FIGS. 6(m) to 6(p) are corresponding experimental images.
FIG. 6(q) is a graph of the crossover movement of the magnetic structure, representing the velocity versus frequency relationship for the movement of the magnetic structure.
Figure 7:
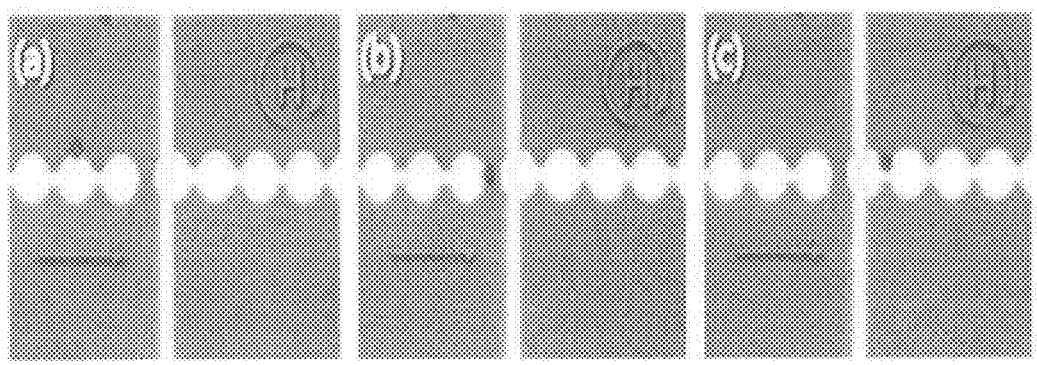
Figure 8:
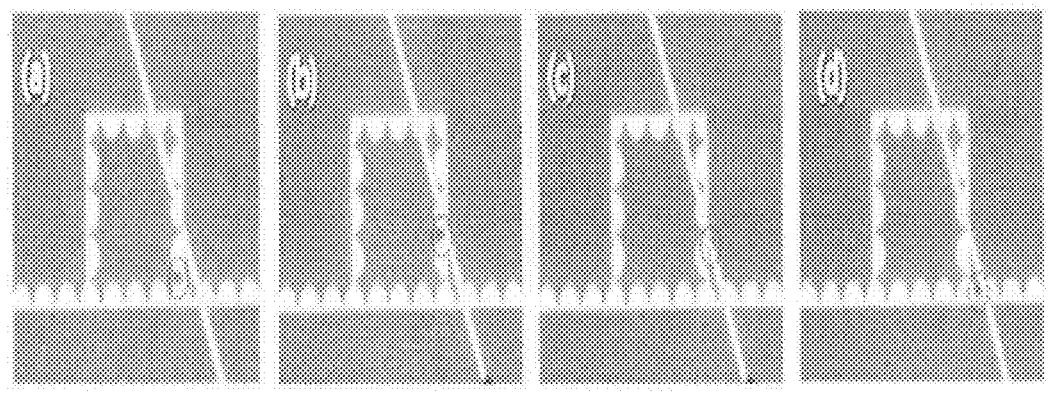
Figure 9:
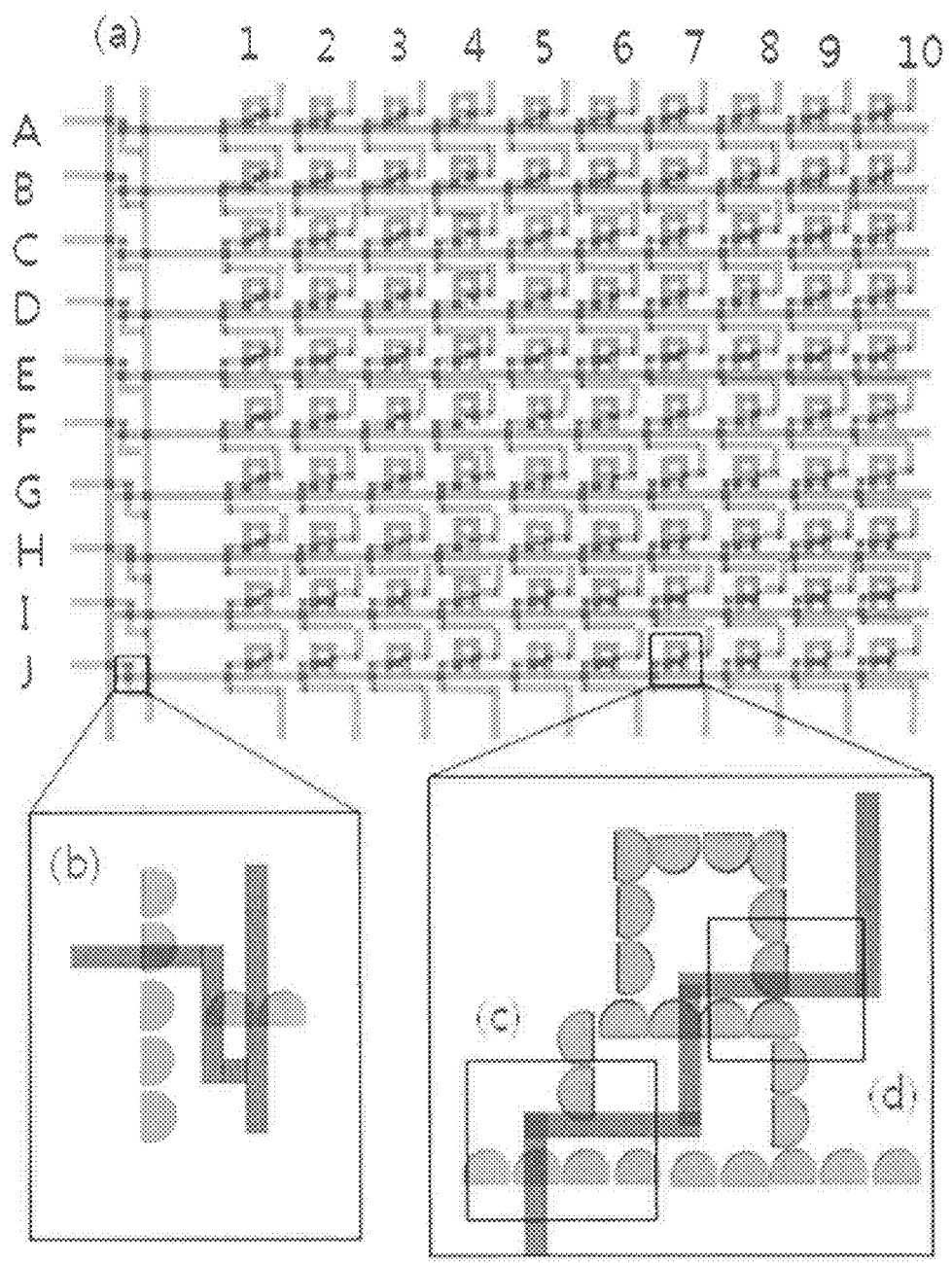

Referring to FIG. 5, the function of field angle (ψ) represents the trajectory of the magnetic structure, in which the increasing angles correspond to the field that is rotating clockwise. Compared to the empirical pathway (see FIGS. 5(e) to 5(h)), the simulation of potential energy distribution (see FIGS. 5(a) to 5(d)) reveals that the position of the magnetic structure is correlated to the shifting regions of the potential energy minima (blue).

The magnetic structures move along the upper section of the track on the outer circumference of the soft magnetic microstructure, because it has the deepest potential energy minima. The linear segment connecting adjacent magnets provides an energy barrier that confines the local energy minima to one side of the magnetic track.

The magnetic structures move exactly by the distance of two half-discs, per rotating cycle of each field. Accordingly, the linear relationship between the oscillation frequency and the flow of magnetic structure ($I_b = \omega/R_b$) behaves in the similar manner as the Ohm's Law of electric flow, as illustrated in FIG. 5 (i) ($I_e = V/R_e$).

At supercritical frequency, the magnetic structures are in the phase-slipping area, where the magnetic structures are periodically oscillated, with decreasing time mean speed.

The clockwise field rotation causes the magnetic structure to move in the positive X-direction, while the counterclockwise rotation causes the magnetic structure to move in the negative X-direction. The soft magnetic microstructures have to be necessarily designed asymmetric, to ensure that net magnetic structure flow is obtained. If the track is circular instead of semicircular, net flow will be negated, which in turn causes the magnetic structures restricted to the lower part of the track to move in the reverse direction from the magnetic structures in the higher part.

Under the clockwise-rotating magnetic field, the magnetic structure moves along the outer circumference of the soft magnetic microstructure of the transporting portion, advances to the positive X-direction, and keeps the linear advancing direction even at an area that adjoins one surface of the storage to crosses over the height of the soft magnetic microstructure to enter the storage. That is, the crossover motion occurs.

More specifically, the magnetic structure has two optional pathways to take, when the magnetic structure reaches the junction between the transporting portion and the storage. One pathway goes along the outer boundary of the storage in a perpendicular direction, and the other maintains the advancing direction by crossover so that the magnetic structure in this pathway moves over the soft magnetic microstructure protruding from the substrate and enter the storage.

Because of relatively lower potential energy of the crossover pathway at the junction between the transporting portion and the storage, the magnetic structure enters into the storage without having a change in the direction and strength of the magnetic field (see FIG. 5).

In one embodiment, the magnetic structure transported into the magnetic structure storage is trapped without escaping the magnetic structure storage as long as the magnetic field maintains strength and direction on the half-disc pattern and magnetic segment pattern which are formed along the inner wall of the storage.

Referring to FIG. 6, FIGS. 6(a) to 6(h) show the magnetic structure trapped into the magnetic structure storage by the crossover motion, in a forward directional mode in the clockwise driving field. The magnetic structure initially moves in the positive X-direction from the left to right sides of the horizontal track. When the magnetic structure arrives at the junction between the transporting portion and the storage, the magnetic structure crosses over the vertical soft magnetic microstructure and continues moving along the curved surface of the horizontal track.

The magnetic structure still crosses over the barrier, thereby minimizing the energy thereof, even when the vertical soft magnetic microstructure has slightly increased potential energy.

The movement according to the energy minima in the periphery of the junction is illustrated in FIGS. 6(b) and 6(c). Regardless of the origin of the magnetic structure flow, the design of the soft magnetic microstructure ensures that the magnetic structure eventually flows along the positive X-direction.

In one embodiment, the magnetic structure transported inside the storage may maintain the magnetic field strength on the half-disc pattern and magnetic segment pattern formed along the inner wall of the storage, but may change the advancing direction when the direction of magnetic field changes.

That is, the magnetic structure may be trapped into the magnetic structure storage and move therein in orbit under the influence of clockwise-rotating magnetic field. Then when the rotating direction of the magnetic field changes to counterclockwise, the direction the magnetic structure move in orbit in the storage is also reversed.

The opposite phenomenon occurs in the counterclockwise driving field. In the initial stage, the magnetic structures move along the outer circumference of the horizontal, soft magnetic microstructure from the right to left sides in the negative X-direction. When the magnetic structure arrives at the junction, the energy barrier applied by the vertical soft magnetic microstructure blocks the magnetic structure from advancing in the negative X-direction.

On the contrary, the magnetic structures change direction to the right and move in the positive Y-direction, which is the lower-change energy pathway.

In one embodiment, the magnetic structure with changed advancing direction is individually controlled, by applying electric current to the magnetic structure transporting portion and the junction and thus changing magnetic field, in which case the magnetic structure is switched to the adjacent transporting portion.

When the distance of the junction of the soft magnetic microstructure is set to be large, the magnetic structure is not transported to the neighboring soft magnetic structure. By forming electric current line in the junction and applying electric current at a minute when the magnetic structure arrives at the junction, planar magnetic field is generated. Then by temporarily changing the entire magnetic field, it is possible to selectively transport, by switching, the magnetic structures.

In one embodiment, the magnetic structure with changed advancing direction may escape the magnetic structure storage, when the magnetic field direction is changed to a direction other than the horizontal plane when the magnetic structure is in the junction between the magnetic structure transporting portion and the magnetic structure storage.

The magnetic structure trapped within the soft magnetic microstructure storage moves in orbit in counterclockwise direction inside the counterclockwise storage, in the magnetic field rotating in counterclockwise direction. It is possible to cause the magnetic structure inside the storage to escape onto the outer circumference of the soft magnetic microstructure of the transporting portion, by temporarily changing the direction of the magnetic field to a direction other than the plane and the horizontal plane on which the substrate is placed, when the magnetic structure arrives at the junction between the transporting portion and the storage.

In one embodiment, it is possible to cause the magnetic structure with changed advancing direction to escape the magnetic structure storage by applying electric current when the magnetic structure is at the junction between the magnetic structure transporting portion and the magnetic structure storage and thus changing the magnetic field.

The magnetic structure trapped within the soft magnetic microstructure storage moves in orbit in counterclockwise direction inside the counterclockwise storage, in the magnetic field rotating in counterclockwise direction. It is possible to cause the magnetic structure inside the storage to escape onto the outer circumference of the soft magnetic microstructure of the transporting portion, by instantly applying electric current when the magnetic structure reaches the junction between the transporting portion and the storage to thus generating planar magnetic field, and temporarily changing the entire magnetic field.

Further, in one embodiment, a soft magnetic microstructure is provided, which includes a magnetic structure transporting portion having a structure formed by a plurality of half-disc patterns and magnetic segment patterns which are connected in series, and a magnetic structure storage having a structure formed by a plurality of half-disc patterns and magnetic segment patterns which are connected in series along an inner wall of a square-shaped disc pattern.

Furthermore, in one embodiment, an apartment-type soft magnetic microstructure is provided, in which an independent magnetic structure transporting portion, formed by a plurality of half-disc patterns and magnetic segment patterns which are connected in series, is connected with a structure having the soft magnetic microstructures at predetermined intervals. Herein, two or more soft magnetic microstructures are connected to each other into an apartment configuration.

Figure 10:
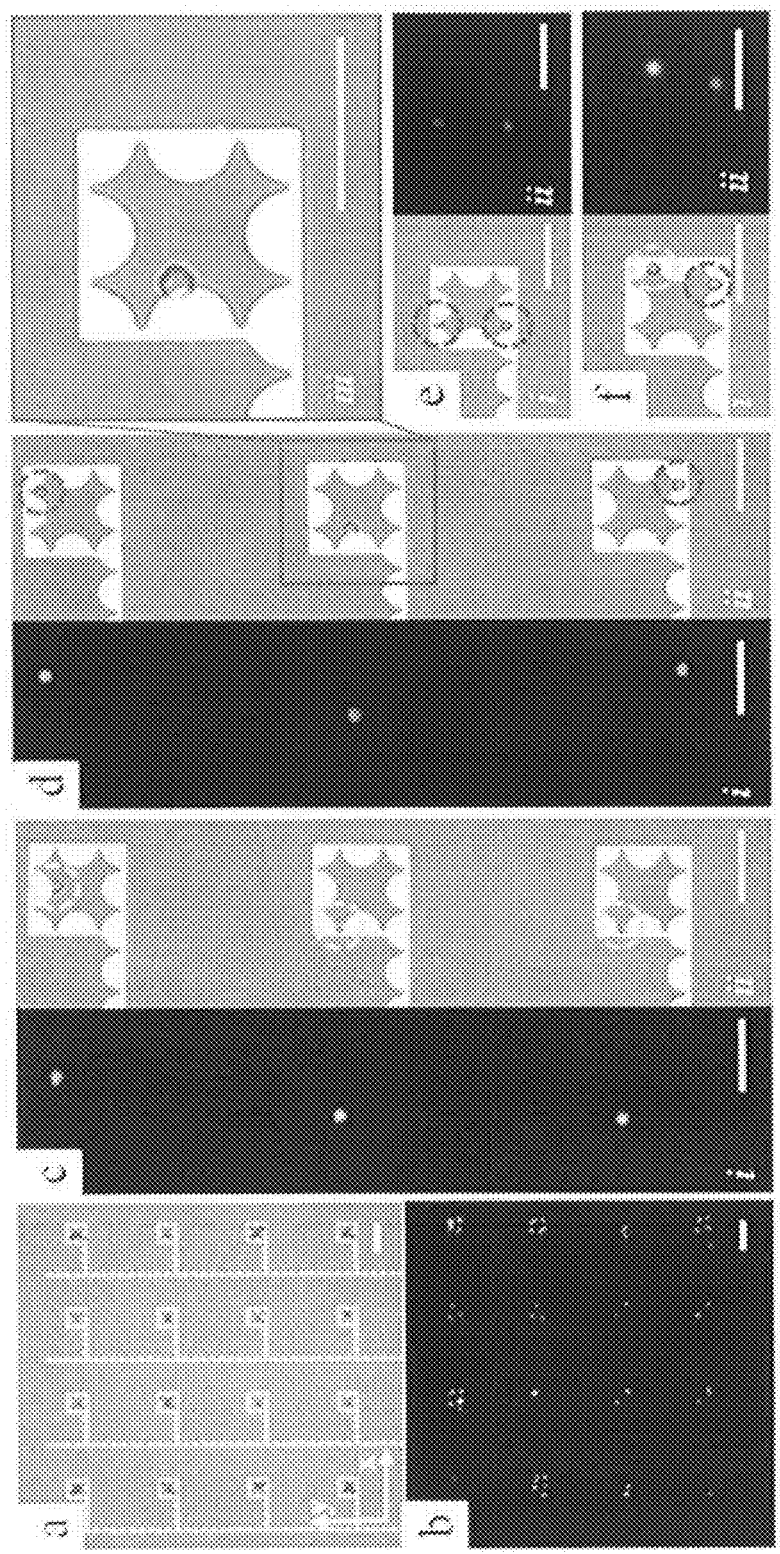
FIG. 10(a) illustrates an apartment type soft magnetic micro structure, FIG. 10(b) are microscopic images of cells shown as the fluorescent spots existing in the apartment type soft magnetic micro structure storage.
FIG. 10(c) shows fluorescent image (i) of T lymphocytes addressed and trapped in the apartment type soft magnetic micro structure storage and bright field image (ii) thereof.
FIG. 10(d) shows fluorescence image (i) of B lymphocytes addressed and trapped in the apartment type soft magnetic micro structure storage and bright field image (ii) thereof, and high resolution bright field image (iii) thereof.
FIG. 10(e) shows bright field image (i) of two B lymphocytes addressed and trapped in a single apartment and fluorescence image (ii) thereof.
FIG. 10(f) shows bright field image (i) of one T lymphocyte and one B lymphocyte addressed and trapped in a single apartment, and fluorescence image (ii) thereof.

Referring to FIG. 10, FIG. 10a particularly shows square-shaped soft magnetic microstructure tracks of the apartments. The field rotating in counterclockwise direction moves the magnetic structures along the vertical tracks to positive Y-direction and along the horizontal tracks to negative X-direction, depending on the initial positions thereof. In the clockwise driving field, the direction of the trajectory is reversed.

When the magnetic structures reach the apartments, they move inside and then trapped in the closed spaces.

However, when the vertical field is utilized, the magnetic structures can escape their apartments as they approach the junction between the transporting portion and the storage in the counterclockwise-rotating magnetic field.

FIG. 10b shows the situation where microorganism is addressed and trapped in the square-shaped soft magnetic microstructure of apartments. The mammalian cell-T (see FIG. 10c) and B lymphocytes (see FIG. 10d) are addressed in predetermined apartments. In this manner, it is possible to address the desired number of the same cells in apartments shown in FIG. 10e (two B lymphocytes) or different cells (B and T lymphocytes) shown in FIG. 10f. Further, it is possible to release the cells from the apartments by applying vertical field when the cells from the counterclockwise direction reach the junction between the transporting portion and the storage.

Further, in one embodiment, a radial soft magnetic microstructure is provided, in which a plurality of magnetic structure transporting portions, with the structure that a plurality of half-disc patterns and magnetic segments patterns are connected in series, are radially aligned, and in which one or more magnetic structure transporting portions are connected to an arbitrary half-disc pattern on the magnetic structure transporting portions.

To be specific, when the rotating magnetic field according to the present invention is applied to the radial type of soft magnetic microstructures, it is possible to induce focusing or defocusing movement of the magnetic structures.

Figure 12:
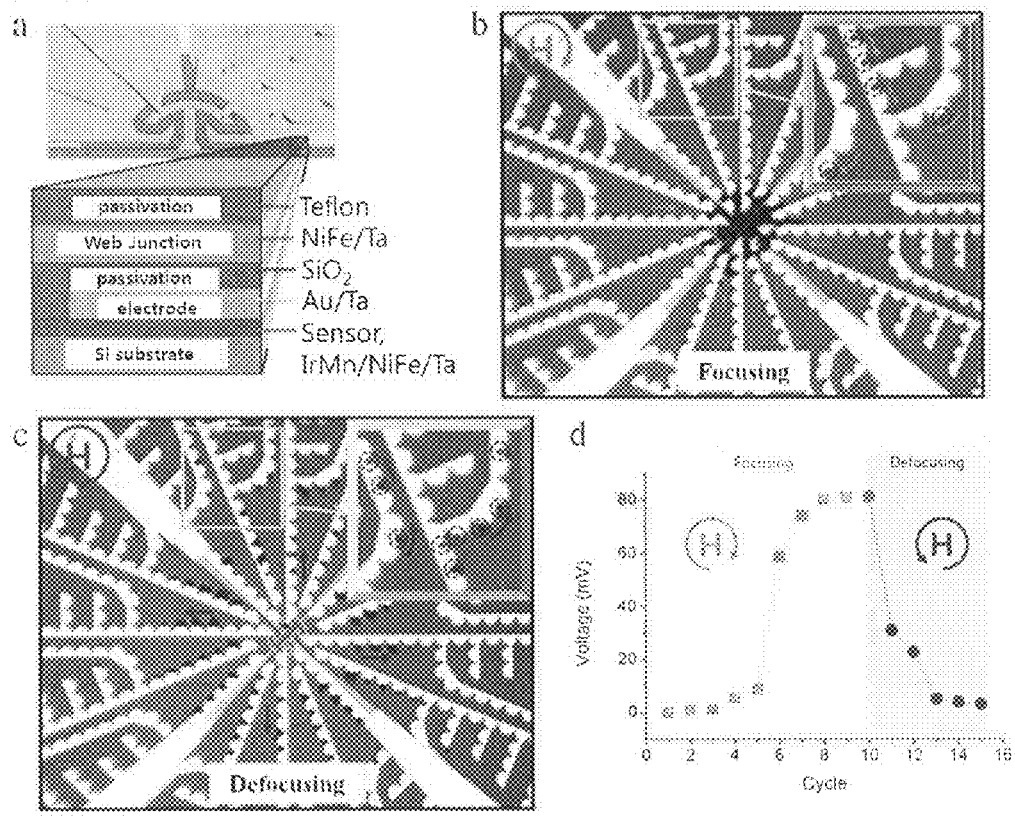

The above-explained ability can strengthen the biosensor which is often hindered by the slow diffusion of the bioanalytes to the sensing region, and especially when the platform for labels or target cells is sub-micron or larger. FIG. 12 shows a lens for focusing matter into a point (i.e., sink), and then diverging matter from that point, which allows for high efficiency sampling of biomolecules near a sensor region.

The lens consists of a plurality of T-junction tracks integrated into a circularly divergent network that resembles a spider web (see FIG. 12). Clockwise rotation of the magnetic field focuses magnetic structures into the center of the lens (see FIG. 12b), whereas counter-clockwise rotation diverges particles away (see FIG. 12c). In a 1 Hz rotating field, nearly all magnetic structures within reach of the matter lens were concentrated at the center node in less than 1 minute.

However, the focusing timescales can be significantly faster, if rotation frequencies higher than 1 Hz are used.

The matter lenses can cover large surfaces and transport matter uniformly from an arbitrary initial position into a small region of space. By contrast, conventional magnetic separation techniques are highly sensitive to the magnetic structure's initial positions (magnetic forces scale as $r^{-7}$).

Figure 13:
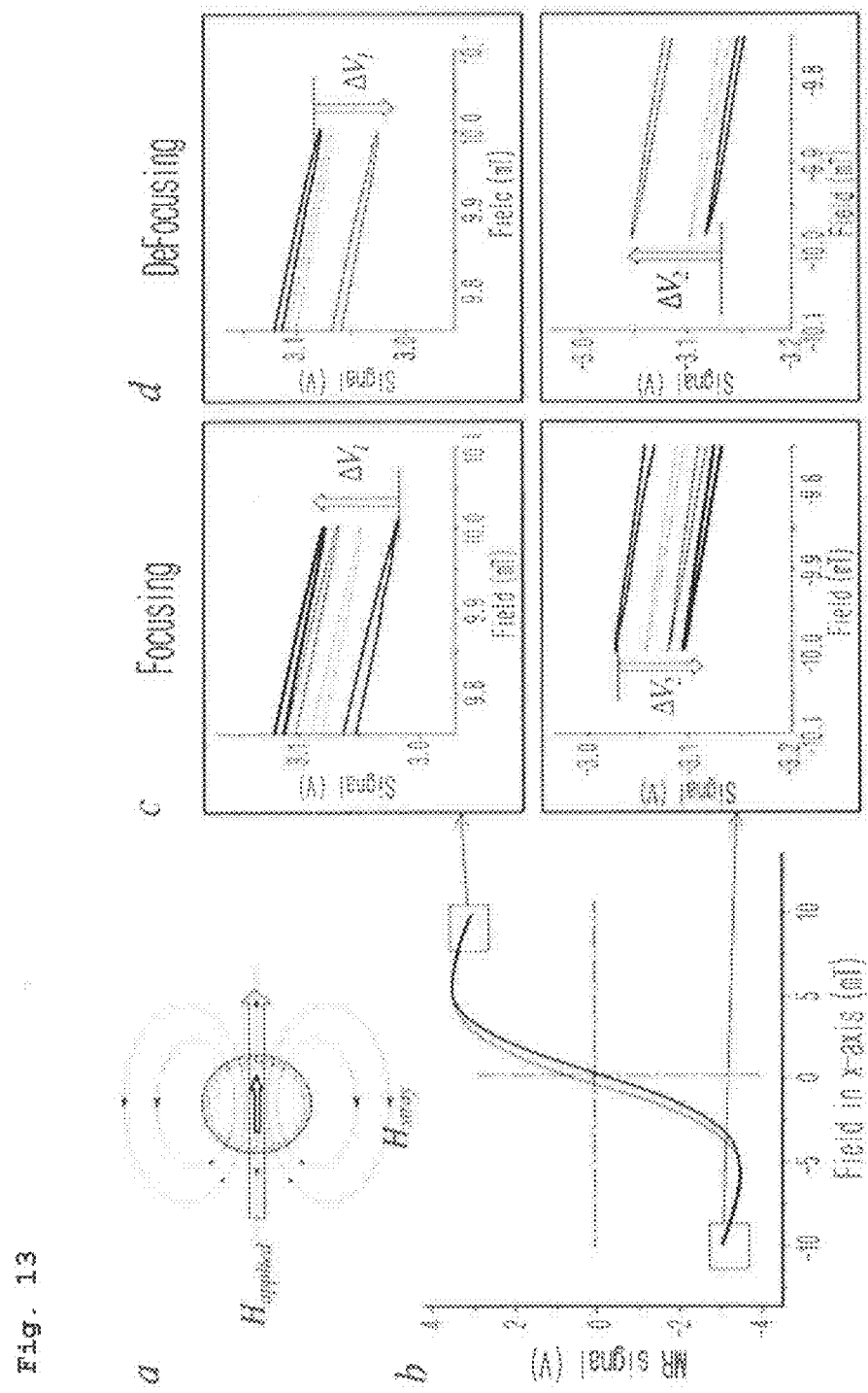
FIG. 13(a) shows the presence of magnetic structure on top surface of the MR sensor leading to stray fields around periphery thereof that opposes the external field.
FIG. 13(b) shows a local field change detected as a change in the voltage versus field relationship.
FIG. 13(c) shows the measured MR signal after 0, 2, 4, 6 cycles of the clockwise rotating field, shown as black, red, blue and pink, respectively.
FIG. 13(d) shows the measured MR signal after 0, 2, 4 cycles of the counter-clockwise rotating field, shown as black, red, and blue, respectively.
Figure 14:
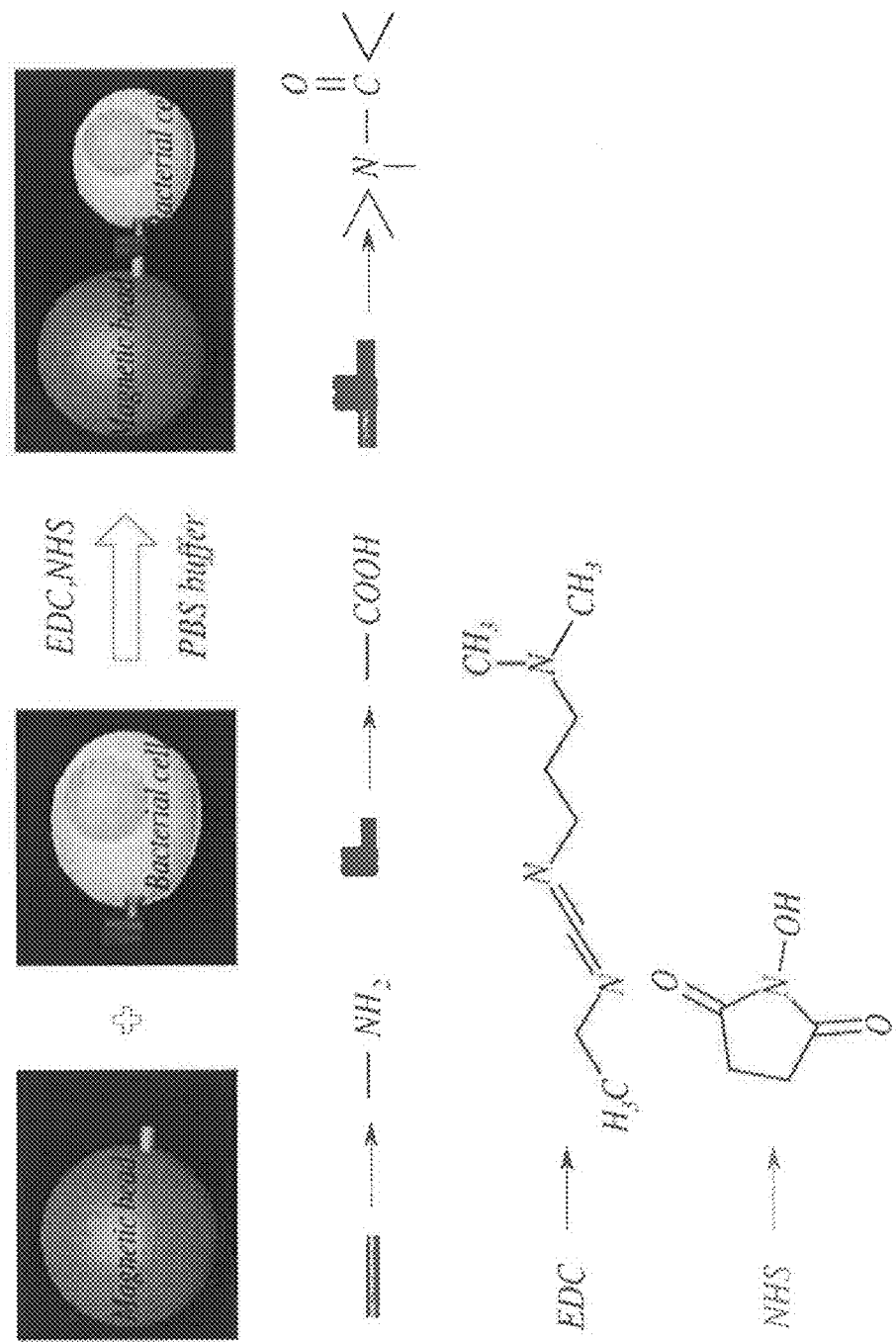
FIG. 14 is a schematic representation of EDC-NHS coupling chemistry used to immobilize microorganisms with magnetic structure.

An integrated matter sensor circuit may be demonstrated by placing a magnetoresistive (MR) sensor at the center node of the spider web, which allows the particle concentration to be monitored as a function of time (see FIGS. 12d, 13). The asymmetry in the time dependence of the sensor signal for the focusing and defocusing pathways reflects the state of initial magnetic structure dispersion. However, it is possible to construct magnetic tracks which could exhibit phenomenologically similar behavior.

In one embodiment, it is possible to induce focusing or defocusing movement of magnetic structures by using the magnetic force generator and the radial type soft magnetic microstructures, and this is utilizable for the purpose of, for example, measuring magnetic characteristics or the like by arranging the central sensor of the magnetoresistive sensor to the center of the radial type soft magnetic microstructures.

FIG. 12 shows a lens circuit including the radial type microstructure for sensing applications, focusing and defocusing magnetic structure under application of clockwise or counter-clockwise rotating magnetic field.

FIG. 13 illustrates the concept of the magnetized magnetic structure present on top surface of the magnetoresistive sensor including the radial type microstructure, leading to stray fields around its periphery that oppose the external field.

In another embodiment, a method for transporting, trapping and escaping single biomaterials is provided, which uses the device for transporting, trapping and escaping the single biomaterial explained above is provided, and which includes:

fabricating a conjugate by reacting a surface-modified magnetic structure with a biomaterial (step 1);

transporting the conjugate along the magnetic structure transporting portion by applying magnetic field to the conjugate fabricated at step 1 (step 2); and trapping the conjugate transported at step 2 in an interior of the magnetic structure storage, while maintaining the strength and direction of the applied magnetic field (step 3).

Each step of the operation according to the present invention will be explained below in detail.

First, step 1 according to the present invention is performed to fabricate a conjugate by reacting surface-modified magnetic structure with biomaterial. That is, at step 1, the magnetic structure, whose surface is modified with functional group such as amino group or carboxyl group, is conjugated with a biomaterial such as biomolecule selected from the group consisting of DNA, protein and virus; bacterial; and cell, by amide binding or ester binding, to thus form a conjugate.

The binding can lead to selective conjugate with antigen-antibody reaction with the biomaterial subject for separation, and it is possible to control the movement of the biomaterial indirectly by way of selective conjugate between the magnetic structure and the biomaterial and movement control.

Next, at step 2, the device for transporting, trapping and escaping single biomaterial according to the present invention is used, in which magnetic field is applied to the device, thus magnetizing the magnetic structure and the soft magnetic microstructure on the substrate, so that the magnetic structure is translocated along the outer circumference of the soft magnetic microstructure on the substrate in a linear direction according to the change in the magnetic field.

FIG. 5 shows magnetic structure trajectory as a function of the field angle ($\psi$), in which the increasing angles correspond to the clockwise rotating field. Compared to the experimental pathways (FIGS. 5e-5h), the simulation (FIGS. 5a to 5d) of the potential energy distribution reveals that the position of the magnetic structure is correlated to the shifting regions of the potential energy minima (blue).

The magnetic structures move along the upper section of the tracks, because it has the deepest potential energy minima. The linear segment connecting adjacent magnets provides an energy barrier that confines the local energy minima to one side of the magnetic track.

The magnetic structures move exactly by the distance of two half-discs, per rotating cycle of each field. Accordingly, the linear relationship between the oscillation frequency and the flow of magnetic structure ($I_b=\omega/R_b$) behaves in the similar manner as the Ohm's Law of electric flow, as illustrated in FIG. 5 (i) ($I_e=V/R_e$).

At supercritical frequency, the magnetic structures are in the phase-slipping area, where the magnetic structures are periodically oscillated, with decreasing time mean speed.

The clockwise field rotation causes the magnetic structure to move in the positive X-direction, while the counterclockwise rotation causes the magnetic structure to move in the negative X-direction. The soft magnetic microstructures have to be necessarily designed asymmetric, to ensure that net magnetic structure flow is obtained. If the track is circular instead of semicircular, net flow will be negated, which in turn causes the magnetic structures restricted to the lower part of the track to move in the reverse direction from the magnetic structures in the higher part.

Next, at step 3, the magnetic structure moving along the transporting portion at step 2 is trapped in the magnetic structure storage whose external contour forms square shape. At step 3, the magnetic structure has two optional pathways to take, when the magnetic structure reaches the junction between the transporting portion and the storage. One pathway goes along the outer boundary of the storage in a perpendicular direction, and the other maintains the advancing direction by crossover so that the magnetic structure in this pathway moves over the soft magnetic microstructure protruding from the substrate and enters the storage.

Because of relatively lower potential energy of the crossover pathway at the junction between the transporting portion and the storage, it is possible that the magnetic structure is induced into the storage and trapped therein.

Referring to FIG. 6, FIGS. 6(a) to 6(h) show the movement of the magnetic structure in a forward directional mode in the clockwise driving field. The magnetic structure initially moves in the positive X-direction from the left to right sides of the horizontal track. When the magnetic structure arrives at the junction between the transporting portion and the storage, the magnetic structure crosses over the vertical soft magnetic microstructure and continues moving along the curved surface of the horizontal track. The magnetic structure still crosses over the barrier and thus minimizes energy thereof, even when the vertical soft magnetic microstructure has slightly increased potential energy thereof. The energy minima on the periphery of the junction are shown in green (FIGS. 5b, 5c). Regardless of the origin of the magnetic structure flow, the design of the soft magnetic microstructure ensures that the magnetic structure eventually flows along the positive X-direction.

The opposite phenomenon occurs in the counterclockwise driving field. In the initial stage, the magnetic structures move along the outer circumference of the horizontal, soft magnetic microstructure from the right to left sides in the negative X-direction. When the magnetic structure arrives at the junction, the energy barrier applied by the vertical soft magnetic microstructure blocks the magnetic structure from advancing in the negative X-direction.

Accordingly, the magnetic structures trapped in the storage do not escape out of the square-shaped soft magnetic microstructure, i.e., the transporting portion, but change direction to the right to thus advance in the positive Y-direction, which is the lower energy pathway.

The present invention will be explained in greater detail below with reference to the Examples.

While the Examples are provided hereinbelow for the illustrative purpose, one will understand that the invention is not limited by any specific Examples.

Example 1

Fabrication of Magnetic Structure Transporting and Trapping Device 2.8-$\mu$m magnetic beads were used in this Example as the magnetic structure, which were Dynabeads M-280 purchased from Invitrogen.

Silicon wafers coated with 200 nm of $SiO_2$ were obtained from Wafermart, and photoresist (AZ 5214-E) and developer were purchased from AZ electronic materials.

To design soft magnetic microstructure, soft permalloy ($Ni_{82.6}Fe_{17.4}$) patterns were fabricated on silicon substrates using conventional photolithographic lift-off method. The magnetic patterns of the soft magnetic microstructure consisted of an array of NiFe thin film type half-discs with 5 $\mu$m radius connected by magnetic segments 2 $\mu$m in length. The soft magnetic microstructure included magnetic structure transporting portion and the storage.

External rotating magnetic field was produced by passing current through pairs of solenoid coils with ferrite cores controlled by LabVIEW (National Instruments). The sense of field rotation was adjusted by applying a phase difference, δ=±90° between the orthogonal coils with field magnitudes ranging from 0 to 15.9 kA/m. Vertical field for the release of the magnetic structures was applied by small electromagnet with square type current.

The magnetic structure transporting and trapping device was fabricated by arranging pairs of solenoid coils on the lower portion of the substrate with the ferrite cores by LabVIEW (National Instruments), and placing the magnetic structures on the surface of the substrate. FIG. 1 is a schematic view of the device.

Example 2

Magnetic Structure Transporting, Trapping and Escaping

The soft magnetic microstructure and magnetic beads (Dynabeads M-280, Invitrogen) deposited on the substrate were magnetized by applying 7.96 kA/m external magnetic field, using the device fabricated in Example 1. After that, the process of generating the clockwise rotating magnetic field and transporting the magnetic beads to the transporting portion and trapping the same in the storage under the magnetic field was tracked by video microscopy such as IMC-1040FT video camera. FIGS. 6e to 6h and FIGS. 6m to 6p present the images captured from the video.

It was observed that the magnetic beads moved along the outer circumference of the half-disc patterns of the soft magnetic microstructure of the transporting portion under the rotating magnetic field, and crossed over the T-type junction between the transporting portion and the storage to enter and be trapped in the storage. The advancing direction of the magnetic beads was maintained, since the external magnetic field was not changed.

After that, to release the trapped magnetic beads back to the transporting portion out of the storage, the direction of the magnetic field was changed by 180°, which in turn change the advancing direction of the magnetic beads inside the storage also by 180°. After that, when the magnetic beads arrived at the junction of the storage with the transporting portion, the direction of the magnetic field was temporarily changed to perpendicular direction. As a result, it was observed that the magnetic beads were released on to the half-disc patterns of the transporting portion (see FIG. 11).

Example 3

Isolation of Positive and Negative Splenocytes from Mouse Spleen

To investigate whether the single cell is isolated or not with the magnetic structure transporting, trapping and escaping device fabricated in Example 1, the following experiment was conducted to isolate positive/negative splenocytes from the mouse spleen.

The magnetic nanoparticles which were 50 nm in diameter, conjugated to CD90.2 (Thy1,2; T lympocyte) and CD45R (B220; B lympocyte), respectively, were purchased from Miltenyi Biotec Inc. (Auburn, Calif., USA).

External rotating magnetic field was produced for application to the device of Example 1 by passing current through pairs of solenoid coils with ferrite cores controlled by LabVIEW (National Instruments). The sense of field rotation was manipulated by applying a phase difference, δ=±90° between the orthogonal coils with field magnitudes ranging from 0 to 15.9 kA/m.

Figure 11:
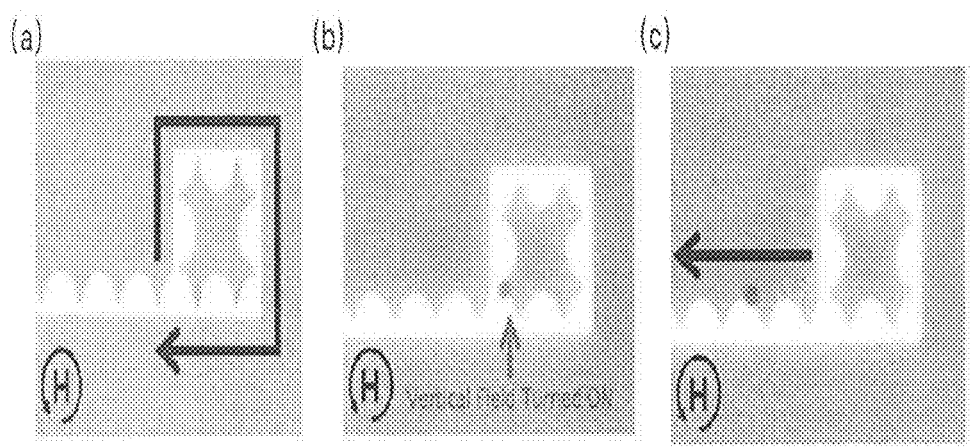
FIG. 11(a) is a video capture showing magnetic structure trapped in the magnetic structure storage and circulating in counterclockwise direction in a counterclockwise-rotating magnetic field.
FIG. 11(b) is a video capture that shows the magnetic structure escaping square storage by the temporary application of magnetic field perpendicular to a plane on which the substrate is present, the moment the internally circulating magnetic structure arrives at a junction with the transporting portion.
FIG. 11(c) is a video capture showing the magnetic structure escaping the storage moving along an outer circumference of the half-disk pattern of the transporting portion.
Figure 15:
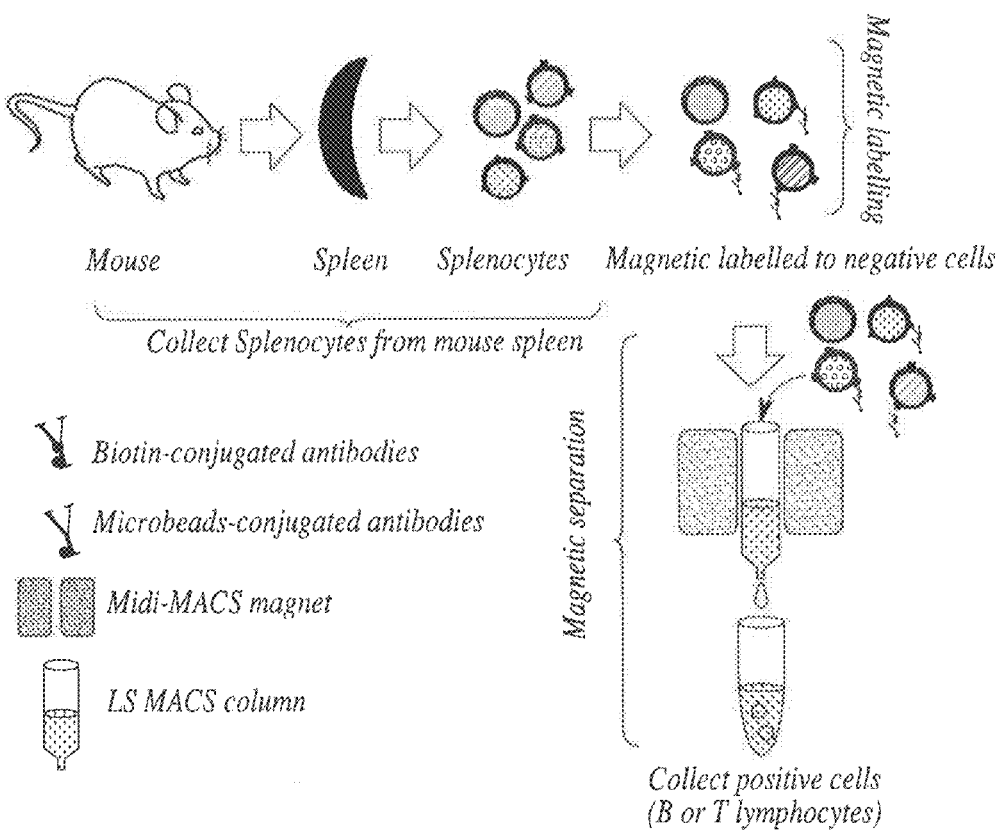
FIG. 15 is a schematic representation for isolation of lymphocytes from mouse through negative magnetic-activated cell sorting (MACS), according to a third embodiment.
Figure 16:
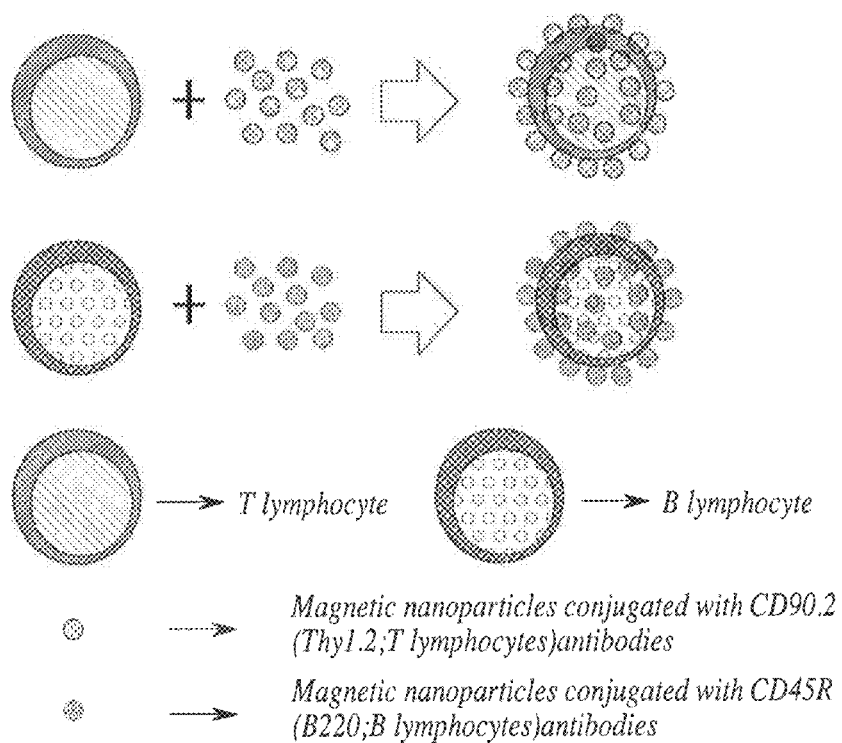
FIG. 16 is a schematic representation of loading magnetic nanoparticles onto lymphocytes used antigen-antibody interaction, according to a third embodiment.

As a result, referring to FIG. 15, it was observed that the magnetic nanoparticles as those illustrated in FIG. 16 were conjugated to the surface of the positive/negative splenocytes in spleen, so that the positive/negative splenocytes were transported and trapped as shown in FIG. 10, and also released as shown in FIG. 11.

DESCRIPTION OF REFERENCE NUMERALS

100: magnetic structure transporting and trapping device system
101: camera
102: substrate
103: soft magnetic microstructure
104: magnetic structure
105: magnetic force generator
106: computer
107: current control device

The invention claimed is:

1. A device for transporting, trapping and escaping a single biomaterial using magnetic structure, comprising:
   a magnetic force generator which applies a magnetic force comprising a direction;
   a soft magnetic microstructure including a magnetic structure transporting portion having a first plurality of half-disc patterns and magnetic segment patterns connected in series,
   a magnetic structure storage having a second, third, and fourth pluralities of half-disc patterns and magnetic segment patterns connected in series, wherein the straight elements of the first, second, third, and fourth pluralities of half-disc patterns form a square shape, and
   a magnetic structure which moves along a curved edge of the first plurality of half-disc patterns and magnetic segment patterns of the magnetic structure transporting portion and the magnetic structure storage of the soft magnetic microstructure,
   wherein the magnetic structure is conjugated with a single biomaterial.

2. The device of claim 1, wherein the magnetic force generator is able to magnetize a soft magnetic microstructure and the magnetic structure, or control strength or direction of a magnetic field formed by the magnetic force.

3. The device of claim 1, wherein the magnetic structure transporting portion and the magnetic structure storage comprise integrally connected patterns to each other or are patterned so that a terminal end at one side of the magnetic structure transporting portion is connected to a terminal end of one side of the storage, to thereby form one complete half-disc form.

4. The device of claim 1, wherein the soft magnetic microstructure is formed by patterning a soft magnetic thin film which comprises any of NiFe, CoFe, NiCo, Fe, Ni, Co or an alloy comprising the same.

5. The device of claim 1, wherein:
   the first plurality of half-disc patterns and magnetic segment patterns comprises a half-disc with a diameter,
   the first plurality of half-disc patterns and magnetic segment patterns comprises a magnetic segment pattern with a length, and a ratio between the diameter of the half-disc and the length of the magnetic segment pattern is 1-10:1.

6. The device of claim 1, wherein the magnetic structure comprises a magnetic bead or a magnetic nanoparticle or is surface-modified to have an antibody bindable by a functional group bindable to a single biomaterial or by antigen-antibody reaction.

7. The device of claim 1, wherein the biomaterial is one selected from a group consisting of biomolecule selected from a group consisting of DNA, protein and virus; bacteria; and cell.

8. The device of claim 1, wherein the magnetic structure binds to the biomaterial to form one type of conjugate selected from a group consisting of magnetic bead-DNA conjugate, magnetic bead-protein conjugate, magnetic bead-virus conjugate, magnetic bead-cell conjugate, magnetic bead-bacteria conjugate, magnetic nanoparticle-cell conjugate and magnetic nanoparticle-bacteria conjugate.

9. The device of claim 1, wherein the magnetic structure under application of a magnetic field formed by the magnetic force moves along the curved edge of the half disc pattern of the magnetic structure transporting portion, and is transported into the magnetic structure storage at a junction with the magnetic structure storage, while maintaining an advancing direction thereof.

10. The device of claim 9, wherein the magnetic structure transported into the magnetic structure storage is not released out of the magnetic structure storage, but trapped therein, as long as the magnetic field maintains the direction on the half disc pattern and the magnetic segment pattern formed along an inner wall of the magnetic structure storage.

11. The device of claim 9, wherein the magnetic structure transported into the magnetic structure storage maintains strength of the magnetic field on the half-disc pattern and the magnetic segment pattern formed along an inner wall of the storage, but changes an advancing direction when the direction of the magnetic field is changed, thereby providing a magnetic structure with a changed advancing direction.

12. The device of claim 11, wherein the magnetic structure with the changed advancing direction escapes out of the magnetic structure storage, when the direction of the magnetic field is changed to a direction other than a horizontal plane as the magnetic structure is at the junction between the magnetic structure transporting portion and the magnetic structure storage.

13. The device of claim 1, wherein the magnetic structure is switched to an adjacent transporting portion and individually controlled, as the magnetic field is controlled in accordance with application of electric current to the magnetic structure transporting portion and a junction between one of the first, second, third, and fourth pluralities of half-disc patterns.

14. The device of claim 1, wherein the magnetic structure with the changed advancing direction escapes out of the magnetic structure storage, when the direction of the magnetic force is changed to a direction other than horizontal plane as the magnetic structure is at a junction between the magnetic structure transporting portion and the magnetic structure storage.

15. The device of claim 1, wherein the magnetic structure escapes out of the magnetic structure storage, as electric current is applied to change the magnetic force, when the magnetic structure is at a junction between the magnetic structure transporting portion and the magnetic structure storage.

16. A soft magnetic microstructure comprising:
a magnetic structure transporting portion having a first plurality of half-disc patterns and magnetic segment patterns connected in series; and
a magnetic structure storage having a second, third, and fourth pluralities of half-disc patterns and magnetic segment patterns connected in series,
wherein:
the straight elements of the second, third, and fourth pluralities of half-disc patterns form a square shape.

17. A method for transporting, trapping and escaping a single biomaterial using the device of claim 1, the method comprising:
fabricating a conjugate by reacting a surface-modified magnetic structure with the biomaterial (step 1);
transporting the conjugate along the magnetic structure transporting portion by applying magnetic field to the conjugate fabricated at step 1 (step 2); and
trapping the conjugate transported at step 2 in an interior of the magnetic structure storage, while maintaining the strength and direction of the applied magnetic field (step 3).

* * * * *